United States Patent
Reiderman

(10) Patent No.: US 9,864,031 B2
(45) Date of Patent: Jan. 9, 2018

(54) MEASUREMENT OF NMR CHARACTERISTICS OF AN OBJECT CONTAINING FAST TRANSVERSAL RELAXATION COMPONENTS

(71) Applicant: Arcady Reiderman, Katy, TX (US)

(72) Inventor: Arcady Reiderman, Katy, TX (US)

( * ) Notice: Subject to any disclaimer, the term of this patent is extended or adjusted under 35 U.S.C. 154(b) by 198 days.

(21) Appl. No.: 14/277,794

(22) Filed: May 15, 2014

(65) Prior Publication Data

US 2016/0018493 A1    Jan. 21, 2016

(51) Int. Cl.
| | | |
|---|---|---|
| *G01R 33/44* | (2006.01) | |
| *G01V 3/14* | (2006.01) | |
| *G01N 24/08* | (2006.01) | |
| *G01R 33/34* | (2006.01) | |
| *G01R 33/38* | (2006.01) | |

(52) U.S. Cl.
CPC ......... *G01R 33/448* (2013.01); *G01N 24/081* (2013.01); *G01R 33/34053* (2013.01); *G01R 33/3808* (2013.01); *G01V 3/14* (2013.01)

(58) Field of Classification Search
CPC ............ G01R 33/448; G01R 33/34053; G01R 33/3808; G01N 24/081
See application file for complete search history.

(56) References Cited

U.S. PATENT DOCUMENTS

2002/0075000 A1*   6/2002   Prammer ................. G01V 3/32
                                                                  324/315
2014/0312896 A1   10/2014   Prussmann

FOREIGN PATENT DOCUMENTS

CH            EP2515131 A1    10/2012

* cited by examiner

*Primary Examiner* — G. M. Hyder

(57) ABSTRACT

Nuclear magnetic resonance properties of a sample containing fast relaxation components are determined using direct detection of the longitudinal component of the nuclear magnetization. Excitation and detection can be performed in different frequency ranges, which enables short dead time of measurements. In some implementations a nuclear magnetic resonance apparatus can be configured for use in oil well logging.

11 Claims, 5 Drawing Sheets

MEASUREMENT OF NMR CHARACTERISTICS OF AN OBJECT CONTAINING FAST TRANSVERSAL RELAXATION COMPONENTS

CROSS-REFERENCE TO RELATED APPLICATIONS

This application is related to a provisional patent application claiming the benefit 35 USC 119(e). The provisional patent application number is 61/830,136; filing date is Jun. 2, 2013.

STATEMENT REGARDING FEDERALLY SPONSORED RESEARCH OR DEVELOPMENT

Not applicable.

BACKGROUND OF THE INVENTION

Field of the Invention

The invention relates generally to the field of measuring nuclear magnetic resonance properties of porous media or biological tissues. More particularly, the invention presents a method of low frequency NMR relaxometry to acquire a total amount of hydrogen in a sample containing a constituent with fast spin-spin NMR relaxation. The fast relaxation constituent could be, for example, kerogen in a core or drill cuttings samples of earth formations or protein in biological samples.

Background Art

NMR relaxation measurements use a static magnetic field to align nuclei in a sample with the direction of the static magnetic field to achieve a thermal equilibrium state characterized by a bulk nuclear magnetization. The rate at which the bulk magnetization is established is described by a spin-lattice relaxation (also called longitudinal relaxation) characterized by a time constant T1. A RF magnetic field orthogonal to the static magnetic field is typically used to disturb the equilibrium state to produce precession of the nuclear magnetization about the static magnetic field. The RF magnetic field is typically applied in a form of short pulses that produce free induction decay signals in an NMR antenna. The decay of the nuclear magnetization in the plane perpendicular to the static magnetic field is associated with a spin-spin relaxation (also called transversal relaxation) characterized by a time constant T2. If the static magnetic field is in Z-direction of Cartesian coordinates, then the transversal component of the nuclear magnetization is in X-Y plane (rotating due to precessional motion of the nuclear magnetization). The spin precession induces in an induction coil—a typical NMR antenna—a sinusoidal signal due to precession of the bulk nuclear magnetization about the static magnetic field with characteristic resonance or Larmor frequency corresponding to the static magnetic field strength. In order for an NMR signal to be induced in the induction coil the coil is adapted to have its sensitivity direction in the X-Y plane. The signal in the NMR antenna is proportional to the density of protons present in the sample. The bulk nuclear magnetization in X-Y plane decays due to reversible (caused by an inhomogeneity of the static magnetic field) and irreversible (true transversal relaxation) processes of de-phasing. The reversibly de-phased spins can be re-phased using refocusing RF pulses, in particular in a form of a standard CPMG sequence.

Acquiring fast spin-spin relaxation components of the NMR signal in the NMR relaxometry is typically limited by the "dead-time" of the measurements. The "dead-time" is typically determined by the RF pulse width and the after-pulse ringing time. Both limiting factors cause the "dead-time" to be inversely proportional to the NMR frequency. Typically, for low field NMR the "dead-time" can be made as short as 0.05 ms. This make the low field NMR measurements well suitable for acquiring NMR relaxation signals from the hydrogen nuclei in liquid constituents of a sample. The liquid constituents typically do not have NMR relaxation times shorter than 0.2 ms. Low field (low Larmor frequency) NMR relaxometry has been successfully used to characterize porous space and fluids in the earth formations (e.g., U.S. Pat. No. 4,717,878, U.S. Pat. No. 5,055,787, and U.S. Pat. No. 6,452,388) as well as other samples including porous samples and biological tissues (e.g., U.S. Pat. No. 6,882,147 and U.S. Pat. No. 7,366,559). It has not been used for analyzing substances containing constituents with spin-spin relaxation times in the microsecond range, for example, for acquiring signature and the total amount of hydrogen in kerogen, or in protein molecules.

Thus known in the art low field NMR relaxometry is not suitable for NMR measurements when the measurement samples contain extremely fast relaxation components, for example, rock samples containing kerogen or biological tissues containing protein. Therefore it is an objective of the present invention to provide a solution for NMR characterization of samples having fast transversal NMR relaxation using low field NMR relaxometry.

BRIEF SUMMARY OF THE INVENTION

One aspect of the present invention is a low frequency NMR relaxometer and measuring techniques for conducting measurements on rock samples (cores, drill cuttings) and biological samples (for in-vivo or in-vitro measurements), the sample containing fast spin-spin relaxation components of NMR relaxation spectrum. The relaxometer comprises a magnet to generate static magnetic field, a RF antenna to generate RF magnetic field in the sample. The RF antenna sensitivity direction (in X-Y plane) is perpendicular to the static magnetic field direction (Z-direction) to generate precession and nutation of the nuclear magnetization about the static magnetic field. The relaxometer also comprises a magnetic field sensor to directly observe a longitudinal component (Z-component) of the nuclear magnetization. In a preferred embodiment the magnetic sensor is an induction coil. The coil has a sensitivity direction parallel to the direction of the static magnetic field to sense variations of the longitudinal component (Z-component) of the nuclear magnetization modified by the RF magnetic field. The signal produced in the induction coil is proportional to time derivative of the Z-component of the nuclear magnetization. RF magnetic field has a carrier frequency equal or close to the Larmor frequency (corresponding to the static magnetic field), which is typically much higher than the main part of frequency spectrum of the Z-component of the nuclear magnetization. Therefore the RF pulse as well as an after-pulse ringing that could interfere with measurements of the X-Y component of the nuclear magnetization does not affect the Z-component measurement. The Z-component signal in the induction coil is used to determine NMR characteristics, in particular, a total amount of hydrogen in a sample containing a constituent with fast spin-spin NMR relaxation.

Another aspect of the present invention is to use an excitation regime that increases the total duration of the Z-component magnetization signal induced in the induction coil and therefore increases signal-to-noise ratio per unit time. In one embodiment the excitation regime described in Nuclear-Magnetic-Resonance Line Narrowing by Rotating RF Field, by M. Lee an W. I. Goldburg is implemented. This excitation regime gives an example of longer lasting Z-component signal variations.

Yet another aspect of the present invention is a side-looking NMR sensor assembly for directly acquiring Z-component of the nuclear magnetization. The sensor is suitable for NMR oil well logging and other NMR measurements requiring an "inside-out" NMR sensor.

Other aspects and advantages of the invention will be apparent from the following description.

BRIEF DESCRIPTION OF THE DRAWINGS

This invention is best understood with reference to the accompanying figures in which like numerals refer to like elements.

DETAILED DESCRIPTION OF THE INVENTION

Figure 1:
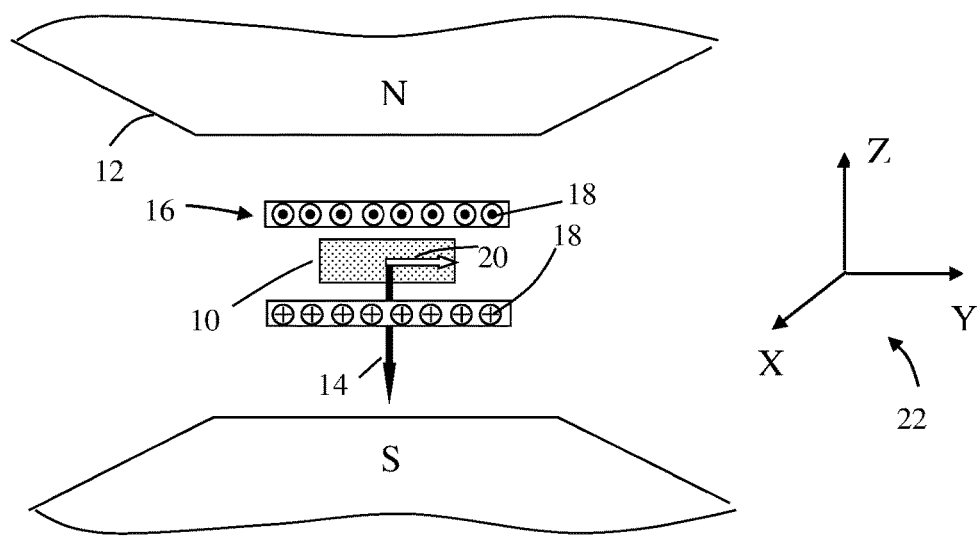
FIG. 1 shows an exemplary embodiment of a standard low field NMR relaxometer of prior art.

FIG. 1 shows an exemplary NMR relaxometer of prior art. It comprises a permanent magnet 12 (shown are the north and the south poles of the magnet) generating a substantially homogeneous static magnetic field 14 in a sample 10, a RF coil 16 generating a RF magnetic field 20 in the sample 10. The arrows 18 show direction of RF current in the antenna wire. In the exemplary embodiment of FIG. 1 the RF coil 16 is used for both generating the RF magnetic field in the sample and receiving NMR signal from the sample. In the Cartesian coordinate system shown at 22 the static magnetic field is in Z-direction, the RF magnetic field and the sensitivity direction of the RF antenna is in Y-direction. The bulk nuclear magnetization (not shown) of the sample undergoes a precessional motion about the direction of the static magnetic field (Z) and therefore has both Y and X components. The NMR relaxometer may have two RF coils with mutually orthogonal sensitivity directions in the X-Y plane.

Figure 2A:
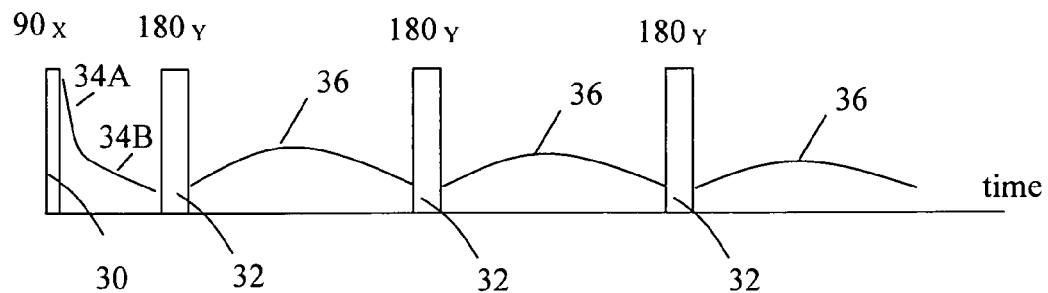
FIG. 2A and FIG. 2B, collectively referred to as FIG. 2, show typical RF pulse sequences used by prior art and illustrate main problems associated with acquiring fast relaxation components of the spin-spin NMR relaxation.
Figure 2B:
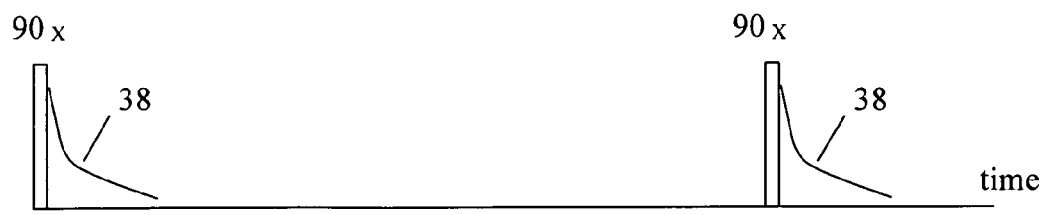

Turning now to FIG. 2, where typical RF pulse sequences used by prior art to measure the amount of hydrogen (or other nuclei) in a sample and the relaxation properties of the nuclei in the sample are presented. A RF pulse flips the nuclear magnetization away from its equilibrium state (Z-direction as shown in FIG. 1). This results in X-Y plane component of the magnetization that directly measured by NMR receiver. The Z-component of the magnetization also changes but this change is not observed by the antenna. Shown on the FIG. 2 are envelopes of RF pulses and the envelopes of the RF nuclear magnetization component in X-Y plane. FIG. 2A depicts CPMG pulse sequence shown at 30 and 32 used to generate a plurality of spin echoes 36, the amplitudes of the echoes as a function of time represent true transversal relaxation curve (not distorted by reversible de-phasing caused by inhomogeneity of the static magnetic field). Also shown in FIG. 2A is a free induction decay signal (FID) after the first 90-degree pulse 30 that flips the nuclear magnetization into the X-Y plane. As shown in the FIG. 2A the FID illustrates the main problem associated with acquiring fast relaxation components of the transversal NMR relaxation. The FID indicates a fast transversal relaxation component 34A and a slow relaxation component 34B. The latter is typically determined by the reversible de-phasing of the nuclear spins. The fast relaxation typically has a characteristic relaxation time in the range 0.01-0.05 ms while the typical time to the first echo (limited by the "dead-time") is more than 0.1 ms. Thus the fast relaxation components irreversibly decay before the first echo is formed. In this case the spin echoes and the transversal relaxation curve do not contain the fast relaxation components. Using FID or a sequence of FIDs shown in FIG. 2B at 38 is generally not practical due to an after-pulse ringing that typically lasts longer than the fast relaxation components to be measured.

Figure 3A:
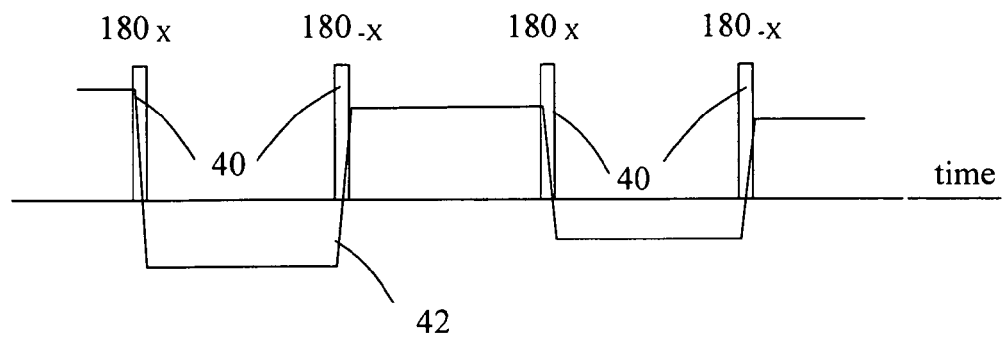
FIG. 3A and FIG. 3B, collectively referred to as FIG. 3, present exemplary RF excitation regimes and the corresponding variations of the Z-component of the nuclear magnetization.
Figure 3B:
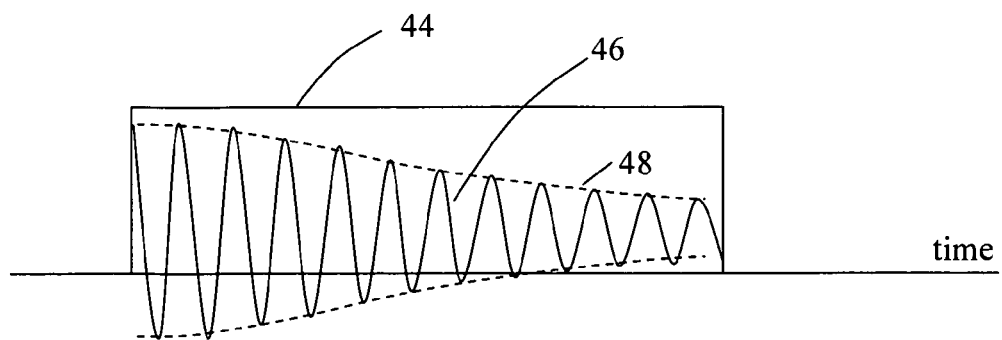
Figure 4:
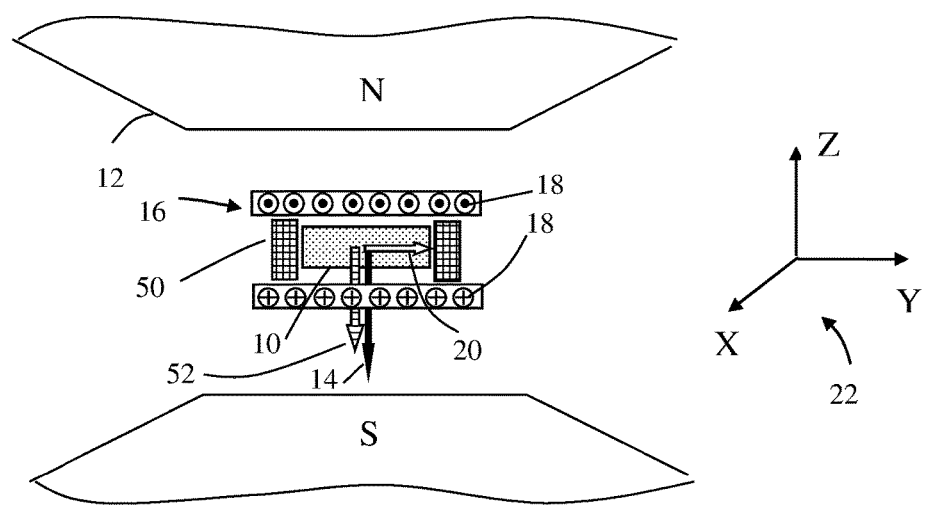
FIG. 4 depicts an exemplary embodiment of NMR relaxometer of present invention.

FIG. 3 gives examples of simple RF pulse sequences suitable for directly acquiring Z-component of the nuclear magnetization. The RF pulses 40 in FIG. 3A (shown at 40 are the envelopes of the RF pulses) are the 180-degree pulses that periodically flip the magnetization from its equilibrium state in +Z direction to the −Z direction and back, thus producing maximum possible changes in the Z magnetization component. The Z-component of nuclear magnetization is shown at 42. Since during this process the magnetization experiences some spin-spin relaxation the change of the Z-component of magnetization gradually decreases. It can be recovered by allowing some waiting time after each 360-degree rotation cycle. It is typical for a constituent with a short spin-spin relaxation time T2 to have a spin-lattice relaxation time T1 that is much greater than T2. Shown in FIG. 3A is the Z-component of the nuclear magnetization corresponding to the case when the distance between the pulses 40 is shorter than the shortest spin-lattice relaxation time of the substance in the sample. FIG. 3B represents response of the Z-component of the nuclear magnetization 46 to a long RF pulse 44 (dashed line 48 demonstrates the envelope of the Z-component of the nuclear magnetization). The FIG. 3B illustrates the excitation regime described in the article Nuclear-Magnetic-Resonance Line Narrowing by Rotating RF Field by M. Lee an W. I. Goldburg, Physical Review volume 140, 1965. As described in the article a certain relationship between the Larmor frequency, the amplitude and the carrier frequency of the RF pulse must be held in order for the Z-component of the nuclear magnetization variations to last almost as long as the spin-lattice relaxation time. It is suggested in the article to measure the Z-component of magnetization existing after the first (long) RF pulse by using a second pulse that flips the Z-component of the magnetization into the X-Y plane and detecting the FID. In a preferred embodiment of the method of present invention the Z-component of the magnetization (reflecting nutation of the nuclear magnetization) is measured directly during the long RF pulse. The excitation regimes presented in FIG. 3 increase the total duration of the Z-component magnetization signal induced in the induction coil and therefore increases signal-to-noise ratio per unit time FIG. 4 depicts an exemplary embodiment of NMR relaxometer of the present invention. It comprises a permanent magnet 12 (shown are the north and the south poles of the magnet) generating a substantially homogeneous static magnetic field 14 in a sample 10, a RF coil 16 generating a substantially homogeneous RF magnetic field 20 in the sample 10. In the exemplary embodiment the RF coil 16 is used for generating the RF magnetic field in the sample. In the Cartesian coordinate system shown at 22 the static magnetic field is in Z-direction, the RF magnetic field and the sensitivity direction of the RF antenna is in Y-direction. The bulk nuclear magnetization (not shown) of the sample undergoes a precessional motion about the direction of the static magnetic field (Z) and therefore has both Y and X components. In order to directly measure the Z-component of the nuclear magnetization $M_Z$ an induction coil 50 is used having the sensitivity direction 52 parallel to the direction of the static magnetic field 14. The voltage induced in the coil 50 is proportional to the time derivative of the Z-component of the nuclear magnetization $dM_Z/dt$. The RF magnetic field generated by the coil 16 has a carrier frequency equal or close to the Larmor frequency, which is typically much higher than the main components in the frequency spectrum of the Z-component of the nuclear magnetization therefore any parasitic signals at Larmor frequency can be filtered out without distorting the main signal of the Z-component. Also the parasitic signals are small because the sensitivity direction of the induction coil 50 is substantially orthogonal to the RF magnetic field generated by the coil 16. Thus the RF pulse as well as the after-pulse ringing that would interfere with measurements of the X-Y component of the nuclear magnetization (prior art) do not affect the Z-component measurement of the present invention. Thus the method of present invention enables acquiring nuclear magnetization data (Z-component of the magnetization) during and immediately after the RF excitation pulses (40 and 44 in FIG. 3) and therefore obtaining NMR magnetization signal corresponding to fast spin-spin relaxation components. The total amount of hydrogen in the sample can be, for example, determined by integrating the voltage induced in the coil 50 and extrapolating the integrated signal to zero time. A narrow band (low noise) reception is preferably implemented to acquire the Z-component signal. For example, if the measurement regime presented in FIG. 3B is implemented, then a narrow band receiver with a central frequency equal to the frequency of nutation of the nuclear magnetization (frequency of oscillation of the Z-component illustrated in FIG. 3B) can be used. Since the coil 50 is used to acquire signal having much lower frequency than the Larmor frequency of the NMR excitation the coil 50 should preferably have larger number of turns than the RF coil 16 in order to provide a required noise matching with a preamplifier used for the Z-component signal reception. It is to be clearly understood that the coil 16 or other coil having sensitivity direction in the X-Y plane can be used to acquire signal proportional to the X-Y components of the nuclear magnetization (for example acquiring CPMG echo train as shown in FIG. 2A) in order to measure NMR relaxation properties of a sample. Combination of the Z-component measurement and the X-Y component measurement enables differentiation between constituents of the sample (e.g. solid or solid-like constituents and liquids). The Z-component measurements to acquire NMR signal that includes fast spin-spin relaxation constituents (e.g. a solid matter) and the X-Y component measurements to acquire relatively slow spin-spin relaxation constituents (liquids) can be run sequentially or during the same CPMG pulse sequence. In case of using the same CPMG sequence the Z-component of the nuclear magnetization is measured during the excitation RF pulse (shown at 30 in FIG. 2A).

It would be readily understood by those skilled in the art that other than the induction coil 50 magnetic sensors can be used to acquire Z-component of nuclear magnetization. For example, a high sensitive atomic magnetometer could be used. In case of using a magnetometer as the magnetic sensor of the Z-component of nuclear magnetization the NMR magnet/antenna assembly (NMR sensor unit) can be placed inside a magnetic screen in order to shield the magnetic sensor from the Earth's magnetic field. It should be understood that only high sensitivity magnetic sensors can be used to acquire Z-component of the nuclear magnetization in low frequency (low field) NMR relaxometry. For example a magnetic sensor described in the patent EP 2 515 131 A1 would not have sufficient sensitivity as applied to the measurements described in the present invention.

Figure 5A:
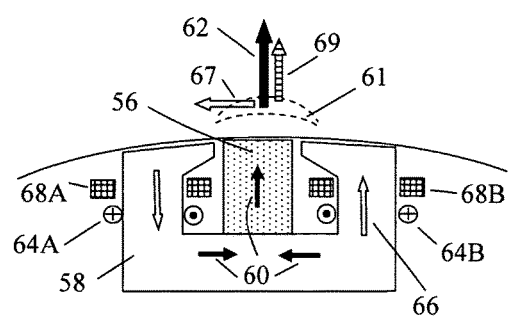
FIG. 5A, FIG. 5B, and FIG. 5C, collectively referred to as FIG. 5, illustrates an exemplary embodiment of magnet and antenna assemblies (side-looking NMR sensors) for high resolution measurement of fast components of NMR relaxation.
Figure 5B:
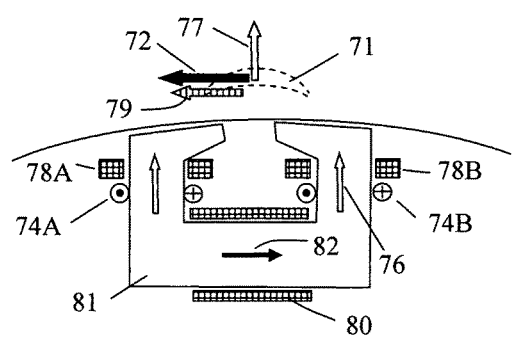
Figure 5C:
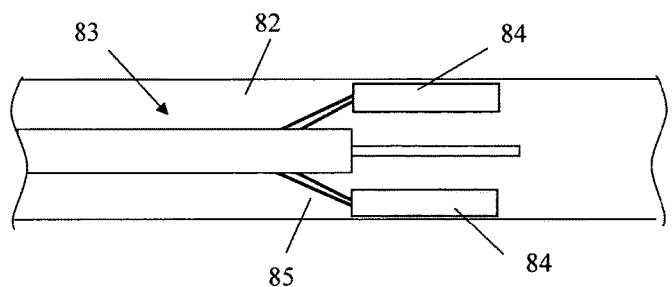

FIG. 5A, FIG. 5B, and FIG. 5C represent another aspect of the present invention: a side-looking NMR sensor, that can be used for NMR well logging. In one embodiment of the sensor shown in FIG. 5A the sensor comprises a source of local static magnetic field represented by a magnet 56 and a soft magnetic core 58. The magnetic flux of the magnet and the static magnetic flux in the core is presented at 60. Magnetic field 62 in the volume of investigation 61 in the earth formations is perpendicular to the axis of the borehole (the borehole axis is perpendicular to the plane of the drawing). The tool axis is parallel to the borehole axis. A radio-frequency magnetic flux in the core is generated by the a RF coil, the two parts of which are shown at 64A and 64B. The radio-frequency magnetic flux direction in the core is shown at 66. The radio-frequency magnetic field 67 at the volume of investigation 61 is perpendicular to the direction of the static magnetic field and also perpendicular to the borehole axis. An induction coil made of two parts 68A and 68B is used to directly acquire signal produced by the Z-component of the nuclear magnetization (Z-component of nuclear magnetization is the component parallel to the static magnetic field 62). The sensitivity direction of the induction coil is shown at 69. In another embodiment of the side-looking sensor shown in FIG. 5B the source of the static magnetic field is formed by a coil 80 and a magnetic core 81. The static magnetic flux direction in the magnetic core is shown at 82. The static magnetic field direction in the volume of investigation 71 is shown at 72. A radio-frequency magnetic flux in the core is generated by a RF coil, the two parts of which are shown at 74A and 74B. The radio-frequency magnetic flux direction in the core is shown at 76. The radio-frequency magnetic field 77 at the volume of investigation 71 is perpendicular to the direction of the static magnetic field and also perpendicular to the borehole axis (the latter is perpendicular to the plane of the drawing). An induction coil made of two parts 78A and 78B is used to directly acquire signal due to Z-component of the nuclear magnetization. The sensitivity direction of the coil is shown at 79.

In both embodiments of the side-looking sensor presented in FIG. 5 the soft magnetic core is made of a magnetically permeable material which is preferably macroscopically non-conductive (e. g. ferrite or stack of thin soft magnetic metal ribbons or tapes separated by insulating layers). The core is used as part of the static magnetic field generation, the radio-frequency magnetic field generation and the nuclear magnetization signal reception subsystems of the sensor. In both embodiments of the side-looking sensor presented in FIG. 5 the RF coils 64A,B and 74A,B can be used for generating the radio-frequency magnetic field in the volume of investigation and also to receive signals produced by X-Y components of the nuclear magnetization (the X-Y components of the nuclear magnetization are the orthogonal components in the plane perpendicular to the static magnetic field). The coils 68 A,B and 78 A,B should preferably have larger number of turns than the RF coils 64A,B and 74A,B in order to provide a required noise matching with a pre-amplifier used for the Z-component signal reception.

FIG. 5C shows a side view of the side-looking sensors representing an exemplary positioning of the sensors. Shown at 83 is a part of the logging tool in the borehole 82. The side-looking sensor 84 is attached to the tool using a retractable arm 85.

The sensors presented in FIG. 5 are configured as a magnetic head-type device with substantially no parasitic NMR excitation in the borehole.

A plurality of sensors presented in FIG. 5 can be used to enable azimuthally selective NMR measurements.

While the invention has been described with respect to a limited number of embodiments, those skilled in the art, having benefits of this disclosure, will appreciate that other embodiments can be devised which do not depart from the scope of invention as disclosed herein.

What I claim as my invention is:

1. A method for making nuclear magnetic resonance measurements of a sample comprising the steps of:
    generating a static magnetic field in the sample to produce a net magnetization of hydrogen nuclear spins in a direction of the static magnetic field;
    generating a radio frequency magnetic field in the sample to produce nutation and precession of the net magnetization;
    detecting a variation of the net magnetization using at least one magnetic probe sensitive to a longitudinal component of the net magnetization, the longitudinal component being collinear with the direction of the static magnetic field, said detecting further comprising using an at least one probe sensitive to a non-longitudinal component of the net magnetization; and
    determining an at least one nuclear magnetic resonance property of the sample based on the variation of the net magnetization, said determining including differentiating between a faster spin-spin relaxation fraction and a slower spin-spin relaxation fraction of the sample based on detecting the longitudinal and the non-longitudinal components of the net magnetization.

2. The method of claim 1 wherein the at least one nuclear magnetic resonance property is a total amount of hydrogen in the sample.

3. The method of claim 1 wherein the magnetic probe is an induction coil sensor.

4. The method of claim 1 wherein a nuclear magnetic resonance signal induced in the induction coil sensor is acquired in a limited frequency band, the frequency band substantially not including an excitation frequency band of the radio frequency magnetic field.

5. The method of claim 4 wherein the radio frequency magnetic field is selected to produce an excitation regime that increases a total duration of the nuclear magnetic resonance signal, the signal induced in the induction coil sensor by a variation of the longitudinal component of the net magnetization, the total duration determining a signal-to-noise ratio of the measurements.

6. The method of claim 1 wherein the radio frequency magnetic field is applied in a form of radio frequency pulses.

7. An apparatus for determining nuclear magnetic resonance properties of a sample comprising:
    a source of static magnetic field to polarize nuclei in the sample;
    a source of excitation magnetic field operable to generate at least one pulse of a radio frequency magnetic field having a direction substantially perpendicular to the direction of the static magnetic field to excite hydrogen nuclei;
    a detection means to acquire nuclear magnetic resonance signals emanating from the hydrogen nuclei excited by the radio frequency magnetic field, the detection means having at least one induction coil sensor with a sensitivity direction being substantially collinear with the direction of the static magnetic field; and
    a processing means to assess a total amount of hydrogen nuclei in the sample.

8. The apparatus of claim 7 wherein the sample contains at least one fraction of the nuclei having a fast spin-spin relaxation time and the at least one pulse of the radio frequency magnetic field has a duration that is substantially shorter than the fast spin-spin relaxation time.

9. The apparatus of claim 7 wherein the nuclear magnetic resonance signals acquired by the sensor have a limited frequency band, the frequency band substantially not overlapping with an excitation frequency band of the radio frequency magnetic field.

10. A method for determining nuclear magnetic resonance characteristics of earth formations surrounding a borehole, comprising the steps of:
    placing a nuclear magnetic resonance logging tool in the borehole;
    applying a static magnetic field to polarize hydrogen nuclei in a downhole region to be analyzed, the hydrogen nuclei being polarized to a thermal equilibrium state, the thermal equilibrium state having a net magnetization parallel to a direction of the static magnetic field;
    applying an at least one pulse of a radio frequency magnetic field to the downhole region to be analyzed to produce a reorientation of the net magnetization therein,
    detecting nuclear magnetic resonance signals caused by the reorientation of the magnetization, the nuclear magnetic resonance signals corresponding to at least two mutually orthogonal components of the magnetization, one of the two components being collinear with the direction of the static magnetic field, the nuclear magnetic resonance signal corresponding to the component collinear with the direction of the static magnetic field being detected using a sensor having a sensitivity direction substantially collinear with the direction of the static magnetic field; and
    processing the nuclear magnetic resonance signals in order to determine a nuclear magnetic resonance characteristic of the earth formations.

11. The method of claim 10 wherein the processing includes using the component collinear with the direction of the static magnetic field to assess a total number of hydrogen nuclei in the downhole region to be analyzed.

* * * * *